(12) United States Patent
Kim et al.

(10) Patent No.: US 10,117,584 B2
(45) Date of Patent: Nov. 6, 2018

(54) MULTI-FUNCTIONAL SENSOR ASSEMBLY

(71) Applicant: Korea Institute of Science and Technology, Seoul (KR)

(72) Inventors: Jinseok Kim, Seoul (KR); Yong-Won Song, Seoul (KR); Jinwoo Jeong, Seoul (KR); Hyowon Moon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 244 days.

(21) Appl. No.: 15/078,180

(22) Filed: Mar. 23, 2016

(65) Prior Publication Data

US 2016/0296122 A1    Oct. 13, 2016

(30) Foreign Application Priority Data

Apr. 9, 2015    (KR) .................. 10-2015-0050092

(51) Int. Cl.
| | |
|---|---|
| *A61B 5/02* | (2006.01) |
| *A61B 5/01* | (2006.01) |
| *A61B 5/026* | (2006.01) |
| *A61B 5/00* | (2006.01) |
| *G01D 5/353* | (2006.01) |
| *A61B 34/20* | (2016.01) |

(52) U.S. Cl.
CPC .............. *A61B 5/01* (2013.01); *A61B 5/0261* (2013.01); *A61B 5/6885* (2013.01); *G01D 5/3538* (2013.01); *G01D 5/35316* (2013.01); *A61B 5/0084* (2013.01); *A61B 2034/2061* (2016.02);

(Continued)

(58) Field of Classification Search
CPC ....... A61B 5/00; A61B 5/0261; A61B 5/6885; G01D 5/35316; G01D 5/3538
See application file for complete search history.

(56) References Cited

U.S. PATENT DOCUMENTS

| | | | |
|---|---|---|---|
| 2010/0114115 A1 | 5/2010 | Schlesinger et al. | |
| 2011/0098533 A1* | 4/2011 | Onoda | A61B 1/0051 600/117 |
| 2011/0177230 A1 | 7/2011 | Sakane et al. | |

(Continued)

FOREIGN PATENT DOCUMENTS

| | | |
|---|---|---|
| KR | 10-2005-0032126 A | 4/2005 |
| KR | 10-1057309 B1 | 8/2011 |

(Continued)

OTHER PUBLICATIONS

Park, Yong-Lae, et al. "Exoskeletal Force-Sensing End-Effectors With Embedded Optical Fiber-Bragg-Grating Sensors." *Robotics, IEEE Transactions on* 25.6 (2009): 1319-1331. (13 pages, in English)

(Continued)

*Primary Examiner* — Paula J Stice
(74) *Attorney, Agent, or Firm* — NSIP Law

(57) ABSTRACT

A sensor assembly has a flexible body, and a plurality of fiber Bragg gratings (FBG) sensor inserted into the body, the FBG sensor includes an optical fiber extending in a length direction of the body and a plurality of lattices disposed in the optical fiber, a variation of a wavelength spectrum of light, caused by a variation of an interval of the plurality of lattices, is detected, and at least one of force information applied to the body and temperature information of the body is extracted together with refraction information of the body.

16 Claims, 6 Drawing Sheets

(52) U.S. Cl.
CPC ............... *A61B 2562/0266* (2013.01); *A61B 2562/0271* (2013.01)

(56) References Cited

U.S. PATENT DOCUMENTS

| | | | |
|---|---|---|---|
| 2012/0323075 A1 | 12/2012 | Younge et al. | |
| 2013/0104672 A1 | 5/2013 | Kim et al. | |
| 2014/0180030 A1* | 6/2014 | Dorando | A61B 5/0215 600/301 |

FOREIGN PATENT DOCUMENTS

| | | |
|---|---|---|
| KR | 10-2012-0050866 A | 5/2012 |
| KR | 10-2013-0015321 A | 2/2013 |
| KR | 10-2013-0049615 A | 5/2013 |
| KR | 10-2013-0092564 A | 8/2013 |
| WO | WO 2012/012565 A1 | 1/2012 |
| WO | WO 2014/043704 A1 | 3/2014 |

OTHER PUBLICATIONS

Park, Yong-Lae, et al. "Real-Time Estimation of 3-D Needle Shape and Deflection for MRI-Guided Interventions." *Mechatronics, IEEE/ASME Transactions on* 15.6 (2010): 906-915. (10 pages, in English).

Moore, Jason P., et al. "Shape Sensing Using Multi-Core Fiber Optic Cable and Parametric Curve Solutions." *Optics Express* 20.3 (2012): 2967-2973. (7 pages, in English).

* cited by examiner

WAVE LENGTH (nm)

MULTI-FUNCTIONAL SENSOR ASSEMBLY

CROSS-REFERENCE TO RELATED APPLICATION

This application claims priority to Korean Patent Application No. 10-2015-0050092, filed on Apr. 9, 2015, and all the benefits accruing therefrom under 35 U.S.C. § 119, the contents of which in its entirety are herein incorporated by reference.

BACKGROUND

1. Field

The present disclosure relates to a sensor assembly, and more particularly, to a sensor assembly capable of loading various sensors with many functions by using an optical fiber.

2. Description of the Related Art

For non-invasive medical treatment, a very thin tubular member such as a medical guide wire becomes more frequently inserted into a blood vessel or the like.

While an instrument such as a guide wire is being inserted into a living body, a worker is not able to see the inserted portion by naked eyes, and thus various measures are being sought for safer and easier insertion.

In an existing technique, two-dimensional photograph information of a blood vessel or the like is obtained by means of radioscopy, and an instrument such as a guide wire is inserted based thereon.

However, the information obtained by means of radioscopy is two-dimensional information, which is not suitable for inserting a guide wire into a blood vessel extending three-dimensionally.

In addition, since it is impossible to obtain any information from the guide wire in relation to the insertion, many problems may occur, and for example, the blood vessel may be damaged due to poor handling.

Moreover, in an existing technique, a catheter should be exchanged and inserted at every operation, which requires a lot of time and technical specialty.

SUMMARY

The present disclosure is directed to providing a multi-functional sensor assembly, which has a minute tubular shape and is inserted into a narrow tubular channel to collect information in relation to a body state such as temperature and force as well as its environments.

In one aspect of the present disclosure, there is provided a sensor assembly, comprising: a flexible body; and a plurality of fiber Bragg gratings (FBG) sensor inserted into the body, wherein the FBG sensor includes an optical fiber extending in a length direction of the body and a plurality of lattices disposed in the optical fiber, wherein a variation of a wavelength spectrum of light, caused by a variation of an interval of the plurality of lattices, is detected, and wherein at least one of force information applied to the body and temperature information of the body is extracted together with refraction information of the body.

According to an embodiment, the force information may be force information applied to a front end of the body, and the temperature information may be temperature information at the front end of the body.

According to an embodiment, the plurality of FBG sensors may include a temperature-detecting FBG sensor for detecting the temperature information, and a front end of the temperature-detecting FBG sensor may be disposed rearward of a front end of the body.

According to an embodiment, the temperature-detecting FBG sensor may be disposed so that a front end portion thereof does not contact the body.

According to an embodiment, the body may have a concave groove formed from the front end thereof, the temperature-detecting FBG sensor may be formed so that the front end portion thereof is located in the concave groove, and the concave groove may have a diameter greater than a diameter of the optical fiber of the temperature-detecting FBG sensor.

According to an embodiment, the plurality of FBG sensors may include a temperature-detecting FBG sensor for detecting the temperature information, and a temperature detection lattice unit having an n (n≥2, natural number) number of lattices with the same interval may be formed at a front end portion of the temperature-detecting FBG sensor.

According to an embodiment, the plurality of FBG sensors may include a force-detecting FBG sensor for detecting the force information, and a front end of the force-detecting FBG sensor may be disposed frontward of a front end of the body.

According to an embodiment, the plurality of FBG sensors may include a force-detecting FBG sensor for detecting the force information, and a force detection lattice unit having an n (n≥2, natural number) number of lattices with the same interval may be formed at a front end portion of the force-detecting FBG sensor.

According to an embodiment, the plurality of FBG sensors may include at least three refraction-detecting FBG sensors for detecting the refraction information, a plurality of lattices may be formed at the refraction-detecting FBG sensor over the entire length of the optical fiber, an n (n≥2, natural number) number of the plurality of lattices may be grouped to form a plurality of refraction lattice units, an n number of lattices may be disposed with the same interval in a single refraction lattice unit, and the refraction lattice units may have different intervals between lattices from each other.

According to an embodiment, the at least three refraction-detecting FBG sensors may be disposed eccentrically from a central axis of the body in a length direction.

According to an embodiment, the plurality of FBG sensors may include: a temperature-detecting FBG sensor for detecting the temperature information; a force-detecting FBG sensor for detecting the force information; and at least three refraction-detecting FBG sensors for detecting the refraction information.

According to an embodiment, the plurality of FBG sensors may include at least three refraction-detecting FBG sensors for detecting the refraction information, at least one of the at least three refraction-detecting FBG sensors may configure a temperature-detecting FBG sensor for detecting the temperature information, and at least another one of the at least three refraction-detecting FBG sensors may configure a force-detecting FBG sensor for detecting the force information.

According to an embodiment, the sensor assembly may further include a laser-irradiating optical fiber inserted into the body to irradiate laser thereto.

According to an embodiment, the sensor assembly may further include a flow sensor inserted into the body to detect flow rate information of a fluid flowing in a work environment at which the body is located.

DETAILED DESCRIPTION

Figure 1:
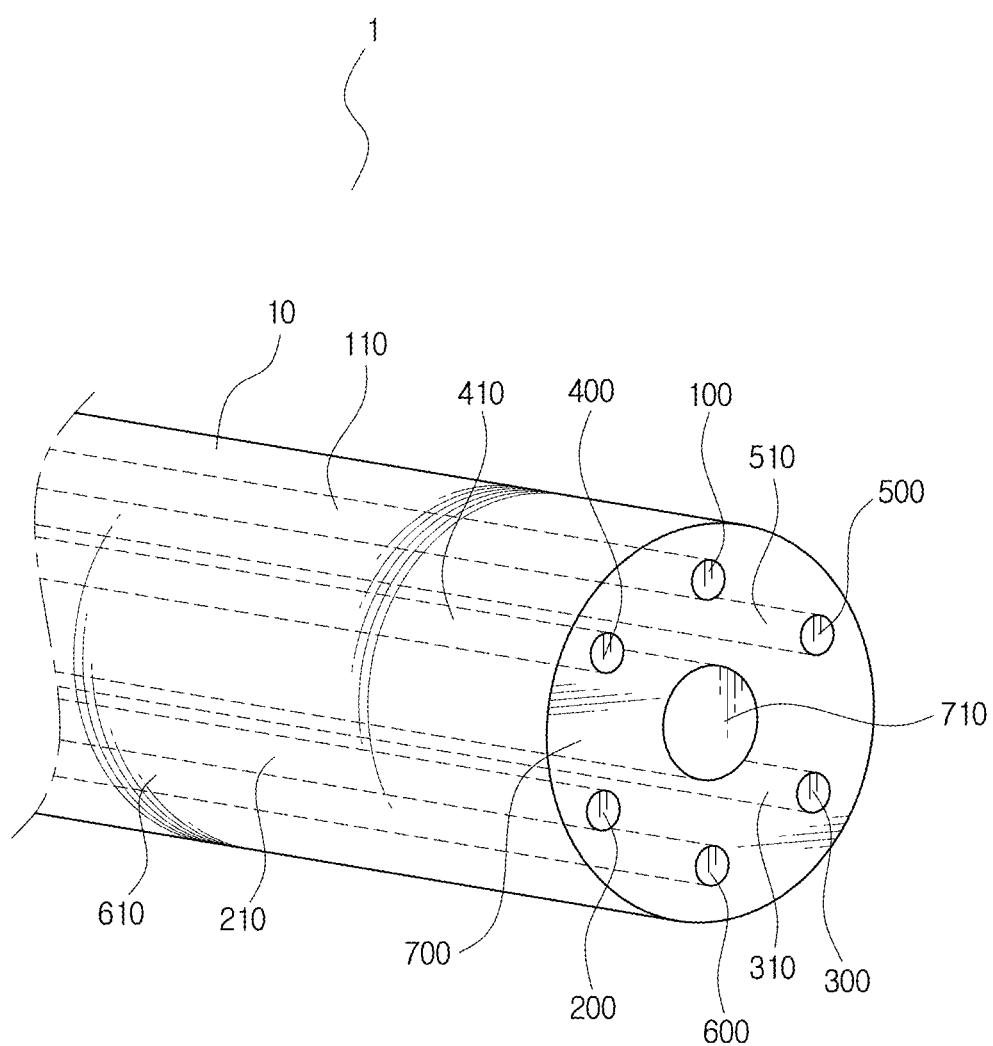
FIG. 1 is a diagram partially showing a sensor assembly according to an embodiment of the present disclosure.

Hereinafter, an embodiment of the present disclosure will be described with reference to the drawings. Even though the present disclosure is described based on the embodiment depicted in the drawings, thus is just an example, and the essential configuration and operations of the present disclosure are not limited thereto.

FIG. 1 is a diagram partially showing a sensor assembly according to an embodiment of the present disclosure.

As shown in FIG. 1, a sensor assembly 1 includes a flexible body 10 extending long, and a plurality of optical fibers 110, 210, 310, 410, 510, 610, 710 inserted into the body 10.

As described later, the plurality of optical fibers 110, 210, 310, 410, 510, 610, 710 may form fiber Bragg gratings (FBG) sensors 100, 200, 300, 400, 500, flow sensor 600 and a laser irradiation path 700.

The sensor assembly 1 of this embodiment may be formed very simply by curing an optical fiber strand, made of glass and surrounded by epoxy.

Even though FIG. 1 illustrates that seven optical fibers are inserted into the body, the structure and number of optical fibers may be adjusted to configure a multi-functional sensor assembly having a desired function selectively.

Figure 2:
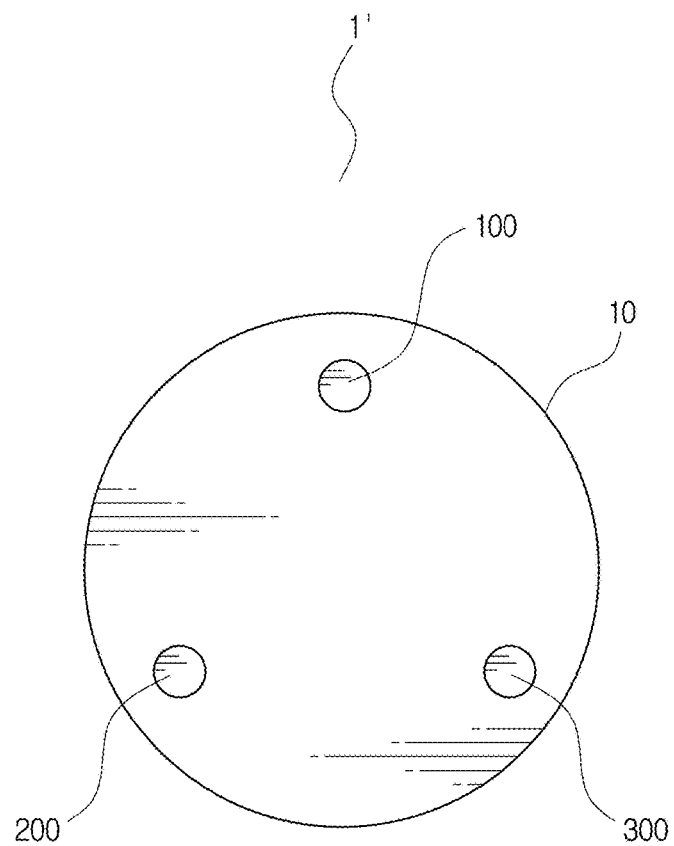
FIG. 2 is a front view showing a sensor assembly according to another embodiment of the present disclosure.

FIG. 2 shows a sensor assembly 1' according to an embodiment of the present disclosure, which has three optical fibers 110, 210, 310.

According to this embodiment, a plurality of lattices is disposed in three optical fibers 110, 210, 310 to configure FBG sensors 100, 200, 300.

Figure 3:
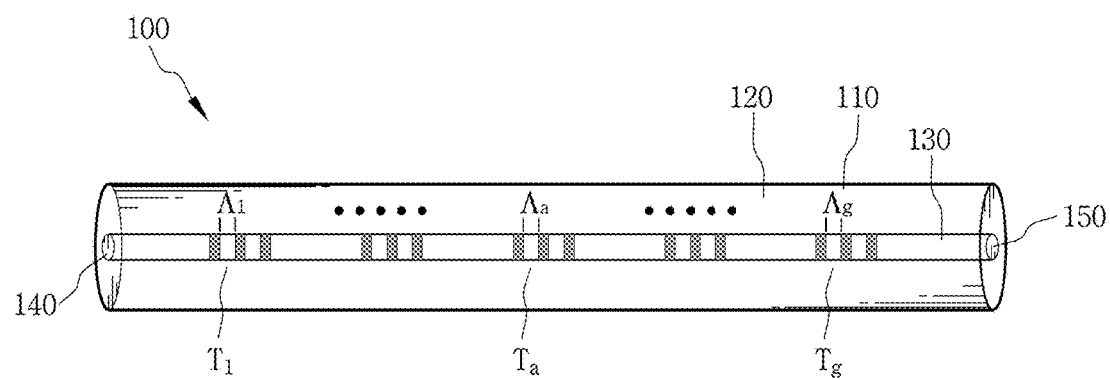
FIG. 3 is a diagram showing a fiber Bragg gratings (FBG) sensor according to an embodiment of the present disclosure.

FIG. 3 conceptually shows a FBG sensor 100 according to this embodiment.

The FBG sensor 100 includes an optical fiber 110 and a plurality of lattices formed in the optical fiber 110.

The optical fiber 110 includes a cladding 120 made of glass material to be freely bendable, a core 130 formed at the center of the cladding 120 along a length direction of the cladding 120. A refractive index of the cladding 120 is different from a refractive index of the core 130. At both ends of the optical fiber 110, a light inlet 140 to which light is incident from a light source (not shown) and a light outlet 150 from which light passing through the core 130 is output are formed.

At the core 130, a plurality of lattice units $T_1$ to $T_g$ is formed, and each lattice unit is formed by grouping at least two lattices.

The lattice is a portion formed by changing properties of a part of the core 130 by means of ultraviolet rays while the optical fiber 110 is being fabricated, and has a refractive index different from the cladding 120 and the core 130.

The lattices forming each lattice unit are disposed with the same interval. Intervals $\wedge_1$ to $\wedge_g$ between lattices of each of the lattice units $T_1$ to $T_g$ are gradually increasing (namely, $\wedge_1 < \ldots < \wedge_a < \ldots < \wedge_g$). The interval between the lattice units is much greater than the intervals $\wedge_1, \ldots \wedge_a, \ldots \wedge_g$ of the lattices which form the lattice units.

In the above configuration, the incident light input to the light inlet 140 of the optical fiber 110 is interfered due to the lattice units. A reflected light output again to the light inlet 140 has a wavelength spectrum with a peak corresponding to each lattice unit.

Figure 4:
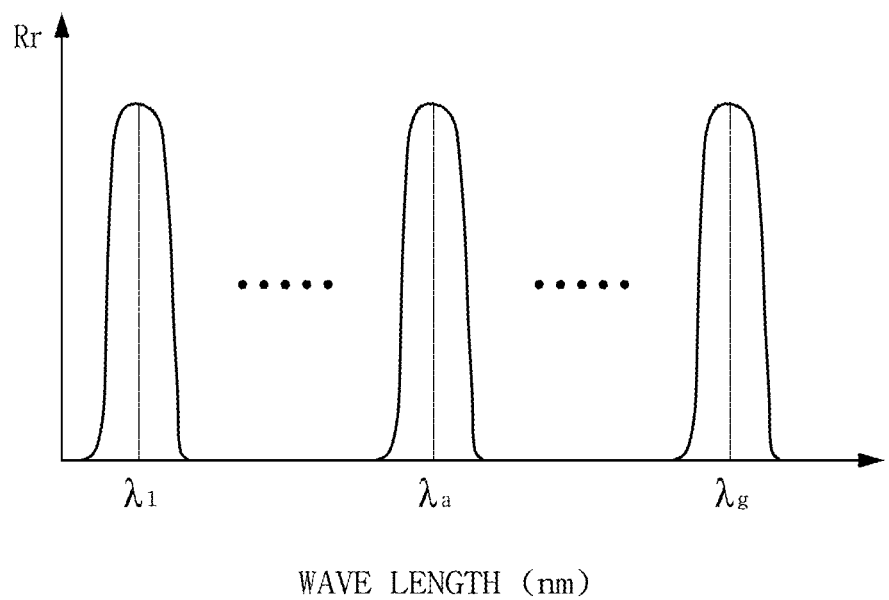
FIG. 4 is a graph showing a wavelength spectrum of a reflected light, output to a light inlet of the FBG sensor of FIG. 3.

FIG. 4 is a graph showing a wavelength spectrum of a reflected light, output to the light inlet 140 of the FBG sensor 100.

A lattice interval $\wedge$ of the lattice unit and a wavelength $\lambda_B$ of the reflected light have a relation as in Equation 1 below.

$$\lambda_B = 2 \cdot n_{eff} \cdot \wedge \qquad \text{Equation 1}$$

Here, $n_{eff}$ is an index representing an effective refractive index of the grating in the fiber core.

The wavelengths $\lambda_1, \ldots \lambda_a, \ldots \lambda_g$ shown in the wavelength spectrum of FIG. 4 correspond to values obtained by putting the intervals $\wedge_1, \ldots \wedge_a, \ldots \wedge_g$ of the lattices of each lattice unit to Equation 1. In other words, the wavelengths $\lambda_1, \ldots \lambda_a, \ldots, \lambda_g$ represent wavelengths of reflected lights which are respectively reflected by corresponding lattice units and output.

When the optical fiber 110 is curved at a portion where a first lattice unit $T_1$ is located, an interval $\wedge_1$ of lattices configuring the first lattice unit $T_1$ will be changed, and accordingly it may be observed that a curve of the wavelength $\lambda_1$ is shifted laterally among the wavelengths of FIG. 4 due to the relation of Equation 1. If it is observed that the curve of the wavelength $\lambda_1$ is shifted laterally, it may be found that the optical fiber is curved at the location of the first lattice unit $T_1$.

As described above, the wavelength $\lambda_B$ of the reflected light output from the FBG sensor 100 and the interval $\wedge$ of the lattice have a proportional relation.

Since the change of the interval $\wedge$ of the lattice represents strain £ of the optical fiber 110, a curvature of the optical fiber 110 may also be found by using the same.

Figure 5:
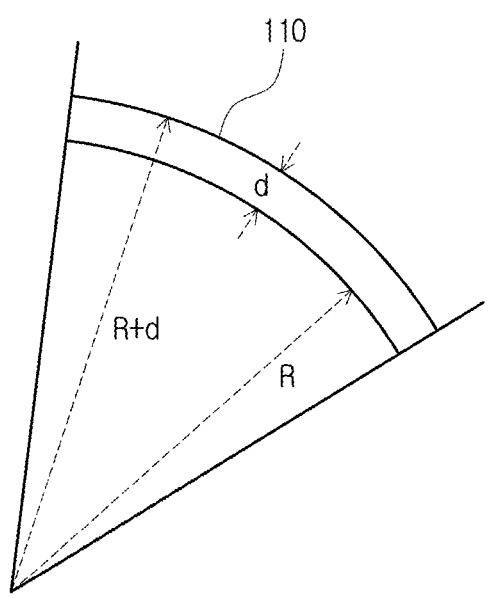
FIG. 5 is a diagram showing that an optical fiber of the FBG sensor of FIG. 3 is partially refracted.

FIG. 5 shows an optical fiber 110 which is partially curved.

As shown in FIG. 5, assuming that a diameter of the optical fiber 110 is d and a curvature of the optical fiber 110 is k (k=1/R), the strain £ of the optical fiber 110 may be expressed like Equation 2 below.

$$\varepsilon = \frac{\Delta L}{L} = \frac{(R+d)\theta - R\theta}{R\theta} = \frac{d}{R} \qquad \text{Equation 2}$$

In the sensor assembly 1', a plurality of FBG sensors having the above characteristics may be formed, and a curvature and a refraction direction of the body 10 of the sensor assembly 1' may be detected using a variation of a wavelength spectrum of the reflected light for each FBG sensor.

Hereinafter, with reference to FIG. 6, a principle of detecting a curvature and a refraction direction of the body 10 will be described.

Figure 6:
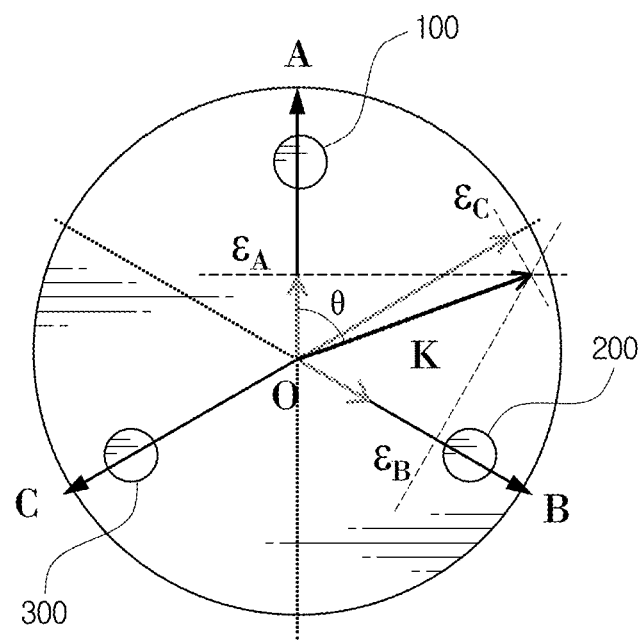
FIG. 6 is a diagram for illustrating the principle of detecting a curvature and a refraction direction of a body at the sensor assembly of FIG. 2.

As shown in FIG. 6, three FBG sensors 100, 200, 300 are formed at the body 10.

Three FBG sensors 100, 200, 300 are disposed radially based on the center O of the body 10 in a length direction and formed with the same interval with an angle of 120° therebetween.

In FIG. 6, for convenience, the FBG sensor 100 is expressed with a subscript A, the FBG sensor 200 is expressed with a subscript B, and the FBG sensor 300 is expressed with a subscript C.

When the body 10 of the sensor assembly 1' is partially curved, a wavelength of a reflected light corresponding to a lattice unit located near each of the FBG sensors 100, 200, 300 is changed.

At this time, depending on a refraction direction, each of the FBG sensors 100, 200, 300 has a different strain £. For example, in FIG. 6, if the body 10 is curved downwards, a lattice unit at a corresponding portion of the FBG sensor 100 will have an increased interval, and lattice units at corresponding portions of the FBG sensors 200, 300 will have a decreased interval.

If comparing strains £ of the FBG sensors 100, 200, 300, a curvature k of the entire body 10 at the curved region may be calculated as in Equation 3 below, and a refraction direction θ may be calculated as in Equation 4.

$$\kappa = \frac{1}{d}\sqrt{\left(\frac{2\varepsilon_A - \varepsilon_B - \varepsilon_C}{3}\right)^2 + \left(\frac{\varepsilon_B - \varepsilon_C}{\sqrt{3}}\right)^2} \quad \text{Equation 3}$$

$$\theta = \operatorname{atan}\left(\frac{\sqrt{3}\,(C_B - C_C)}{2\varepsilon_A - \varepsilon_B - \varepsilon_C}\right) \quad \text{Equation 4}$$

Here, $£_A$ is a strain of the FBG sensor 100 at the refraction portion, $£_B$ is a strain of the FBG sensor 200 at the refraction portion, and $£_C$ is a strain of the FBG sensor 300 at the refraction portion.

If wavelength spectrums of the reflected lights respectively output from the FBG sensors 100, 200, 300 of the sensor assembly 1' are analyzed, a portion of the body 10 which is curved and a strain at the portion may be found, and also a curvature and a refraction direction of the body 10 may be found using Equations 3 and 4.

In this specification, a refraction occurrence point, a curvature and/or a refraction direction of the body 10 will be defined as refraction information of the body 10.

Meanwhile, even though it is detected that a wavelength is changed at a location of any one lattice unit in the wavelength spectrums of reflected lights respectively output from the FBG sensors 100, 200, 300, if the curvature k and the refraction direction θ at the corresponding portion are calculated to be substantially 0 (zero), this wavelength variation may be regarded as being caused by a length variation of the optical fibers of the FBG sensors 100, 200, 300 according to a temperature variation.

Since the body 10 of the sensor assembly 1' is so thin to be inserted into a blood vessel of a living body, the locations of the FBG sensors 100, 200, 300 are very close to each other.

Therefore, the temperature at a portion where a wavelength variation is detected may be calculated as in Equation 5 below, which corresponds to an average value of strains of three FBG sensors 100, 200, 300.

$$\Delta T = \frac{\varepsilon_A + \varepsilon_B + \varepsilon_C}{3\alpha} \quad \text{Equation 5}$$

Here, α is a temperature coefficient of the optical fiber.

However, the temperature of Equation 5 should be calculated on the assumption that lattice intervals of the FBG sensors 100, 200, 300 are not changed, except for temperature.

In addition, if it is intended to use the sensor assembly 1' for an invasive treatment instrument such as an embolic treatment instrument, it is required to accurately figure out a temperature of the front end of the body 10, rather than an intermediate portion of the body 10.

Therefore, a sensor assembly 1" according to another embodiment of the present disclosure is configured to detect temperature information of the front end of the body 10 by using the FBG sensor 100.

Figure 7:
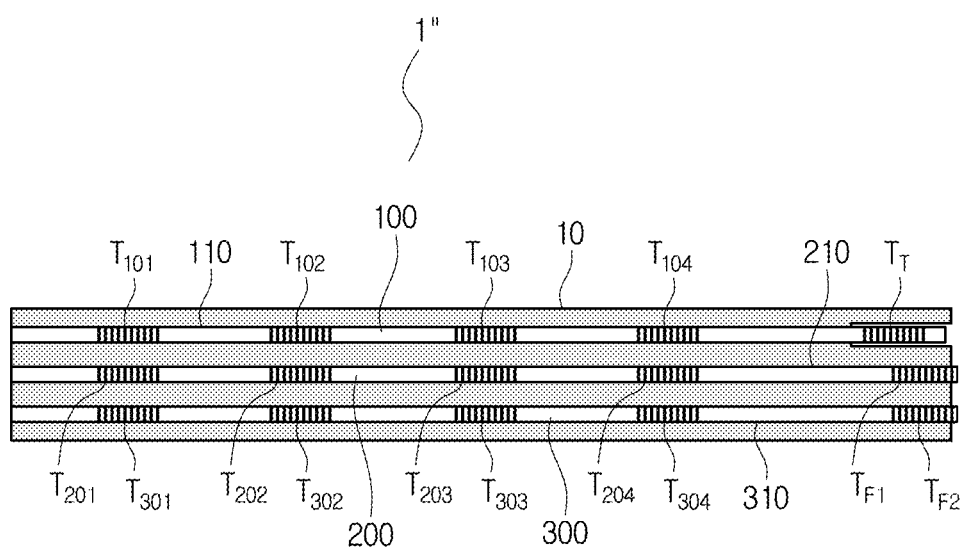
FIG. 7 is a side view showing a sensor assembly according to another embodiment of the present disclosure.
Figure 8:
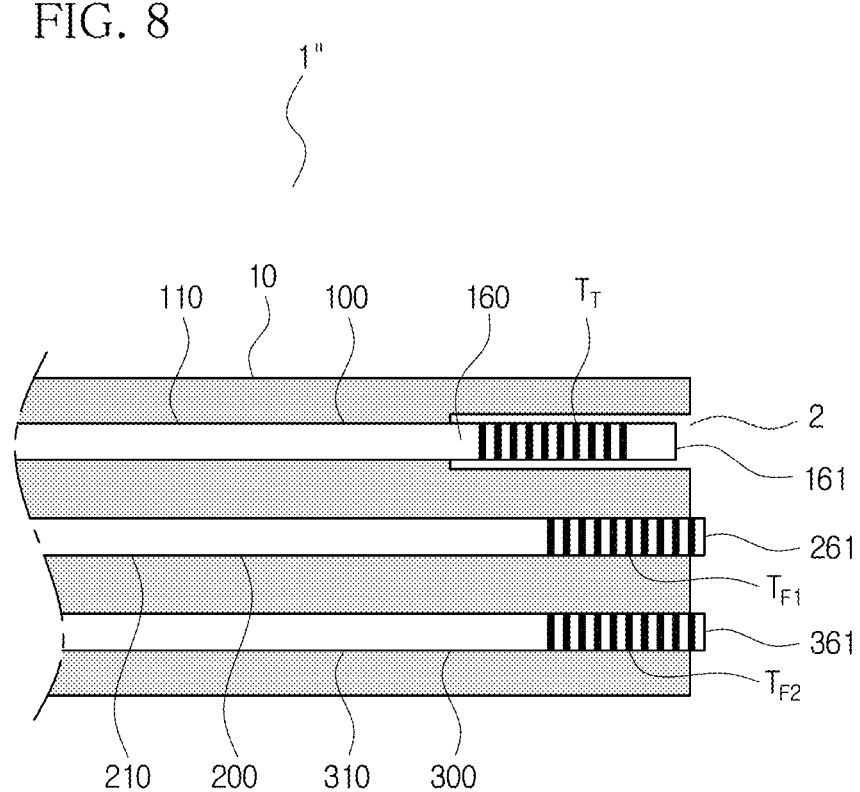
FIG. 8 is an enlarged view showing a front end portion of the sensor assembly of FIG. 7.
Figure 9:
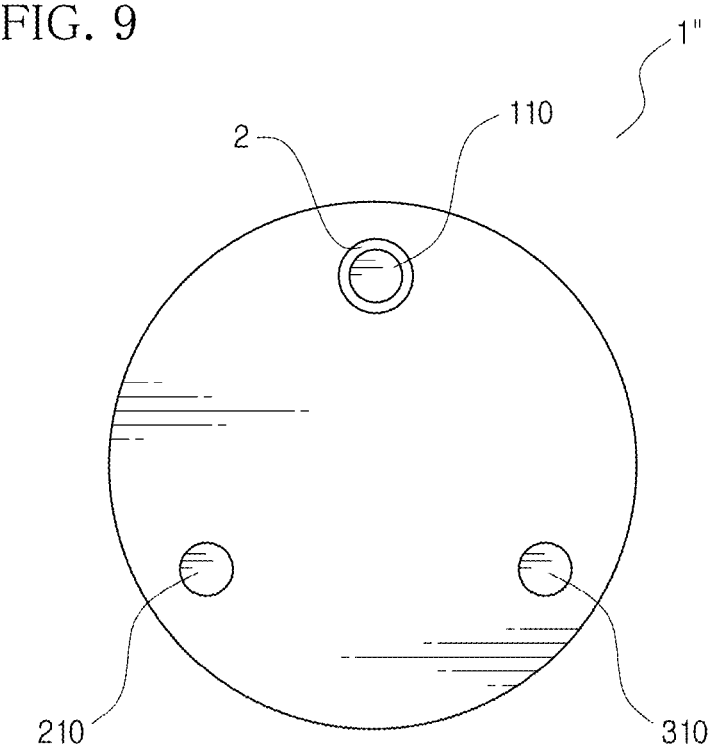
FIG. 9 is a front view showing the sensor assembly of FIG. 7.

FIG. 7 is a side view showing the sensor assembly 1" of this embodiment, FIG. 8 is an enlarged view showing a front end portion of the sensor assembly 1", and FIG. 9 is a front view showing the sensor assembly 1".

As shown in FIGS. 7 to 9, the sensor assembly 1" includes three FBG sensors 100, 200, 300. For convenience, three FBG sensors 100, 200, 300 are disposed without distinguishing an optical fiber and a core.

A plurality of refraction lattice units $T_{101}$, $T_{102}$, $T_{103}$, $T_{104}$ is formed in the middle of the optical fiber 110 of the FBG sensor 100. Lattices forming each of the refraction lattice units $T_{101}$, $T_{102}$, $T_{103}$, $T_{104}$ are disposed with the same interval. Intervals of lattices forming each of the refraction lattice units $T_{101}$, $T_{102}$, $T_{103}$, $T_{104}$ are different from each other and are gradually increasing in this embodiment.

A plurality of refraction lattice units $T_{201}$, $T_{202}$, $T_{203}$, $T_{204}$ is formed in the middle of the optical fiber 210 of the FBG sensor 200. Lattices forming each of the units $T_{201}$, $T_{202}$, $T_{203}$, $T_{204}$ are disposed with the same interval. Intervals of lattices forming each of the units $T_{201}$, $T_{202}$, $T_{203}$, $T_{204}$ are different from each other and are gradually increasing in this embodiment.

A plurality of refraction lattice units $T_{301}$, $T_{302}$, $T_{303}$, $T_{304}$ is formed in the middle of the optical fiber 310 of the FBG sensor 300. Lattices forming each of the refraction lattice units $T_{301}$, $T_{302}$, $T_{303}$, $T_{304}$ are disposed with the same interval. Intervals of lattices forming each of the units $T_{301}$, $T_{302}$, $T_{303}$, $T_{304}$ are different from each other and are gradually increasing in this embodiment.

If a wavelength variation of a reflected light of each sensor corresponding to the refraction lattice units of three FBG sensors 100, 200, 300 is detected, refraction information of the body 10 may be obtained.

Meanwhile, a temperature detection lattice unit $T_T$ composed of at least two lattices is formed at the front end portion of the optical fiber 110 of the FBG sensor 100. An interval of the lattices forming the temperature detection lattice unit $T_T$ is different from intervals of lattices respectively forming the refraction lattice units $T_{101}$, $T_{102}$, $T_{103}$, $T_{104}$.

The temperature detection lattice unit $T_T$ is not formed in a different way from the refraction lattice units $T_{101}$, $T_{102}$, $T_{103}$, $T_{104}$, but just its location and lattice interval are different therefrom.

In order to measure an accurate temperature of the front end portion of the body 10, the temperature detection lattice unit $T_T$ is configured to minimize factors which change the lattice interval, except for a length variation of the optical fiber caused by temperature.

For this, the body 10 includes a concave groove 2 formed from its front end with a regular depth. The front end portion 160 of the FBG sensor 100 is disposed to be located in the concave groove 2. The concave groove 2 has a diameter greater than a diameter of the optical fiber 110 so that the front end portion 160 of the FBG sensor 100 has a free end without contacting the body 10.

In this specification, the "front end portion of the FBG sensor" may also be defined as a length portion including a lattice unit located at a foremost side, among lattice units provided at the FBG sensor.

In addition, according to this embodiment, the front end 161 of the FBG sensor 100 is disposed inwards (rearwards) in comparison to the front end of the body 10.

In this configuration, the front end portion 160 of the FBG sensor 100 may be regarded as substantially changing its length only by a temperature variation, without being influenced by a contact and/or bending of the front end of the body 10.

If a length variation occurs at the front end portion 160 of the FBG sensor 100, the lattice interval of the temperature detection lattice unit $T_T$ is changed, and also a wavelength of a reflected light corresponding to the temperature detection lattice unit $T_T$ is changed.

A peak corresponding to the wavelength of the reflected light corresponding to the temperature detection lattice unit $T_T$ may be figured out among various peaks of the reflected light output through the light inlet of the FBG sensor 100, as described above.

A strain $\varepsilon_T$ of the temperature detection lattice unit $T_T$ may be obtained by means of a wavelength variation of the reflected light corresponding to the temperature detection lattice unit $T_T$, and a variation of temperature T corresponding thereto may be figured as in Equation 6 below.

$$\Delta T = \frac{\varepsilon_T}{\alpha} \quad \text{Equation 6}$$

Here, $\alpha$ is a temperature coefficient of the optical fiber 110 of the FBG sensor 100.

Meanwhile, according to this embodiment, the FBG sensor 200 includes a force detection lattice unit $T_{F1}$ composed of at least two lattices at a front end portion thereof in order to detect information about a force applied to the front end of the body 10.

An interval of lattices forming the force detection lattice unit $T_{F1}$ is different from intervals of lattices respectively forming the units $T_{201}$, $T_{202}$, $T_{203}$, $T_{204}$. The force detection lattice unit $T_{F1}$ is not formed in a different way from the units $T_{201}$, $T_{202}$, $T_{203}$, $T_{204}$, but only its location and lattice interval are different therefrom.

The front end portion of the FBG sensor 200 is mostly confined by the body 10, but its front end 261 protrudes forwards in comparison to the front end of the body 10.

Accordingly, the front end 261 of the FBG sensor 200 comes into contact with an article in advance in comparison to the front end of the body 10.

If the front end 261 of the FBG sensor 200 comes into contact with an article or obstacle, the front end 261 of the FBG sensor 200 is pressed, and the interval between lattices of the force detection lattice unit $T_{F1}$ is decreased.

By detecting a wavelength variation of the reflected light corresponding to the force detection lattice unit $T_{F1}$ according to the above, it may be found whether the front end of the sensor assembly 1" makes a contact.

Further, since a strain ε of the front end portion of the FBG sensor 200 may be figured out, an accurate force F may also be calculated using Equation 7 below.

$$\varepsilon = \frac{\Delta L}{L} = \frac{\sigma}{E} = \frac{F}{E_S A} \quad \text{Equation 7}$$

Here, $E_s$ is a Young's modulus of the sensor assembly 1", and A is an area of the front end of the body 10.

In the sensor assembly 1", since the body 10 is made of epoxy and the optical fiber is made of glass material, the Young's modulus $E_s$ of the sensor assembly 1" may be defined as in Equation 8 below.

$$E_S = (E_G A_G + E_E A_E)/(A_G + A_E) \quad \text{Equation 8}$$

Here, $E_G$ is a Young's modulus of glass, $E_E$ is a Young's modulus of epoxy, $A_G$ is an area of the glass, and $A_E$ is an area of the epoxy.

In this configuration, it may be found whether the front end of the body 10 makes a contact, and an intensity of the contact force may be found, by means of the FBG sensor 200.

In this specification, the information about whether the front end of the body 10 makes a contact and/or about intensity of the contact force are defined as force information applied to the body 10.

Meanwhile, according to this embodiment, in order to detect the force information applied to the body 10 more broadly or more accurately, a force detection lattice unit $T_{F2}$ composed of at least two lattices is also formed at the front end portion of the FBG sensor 300.

An interval of the lattices forming the force detection lattice unit $T_{F2}$ is different from intervals of lattices respectively forming the refraction lattice units $T_{301}$, $T_{302}$, $T_{303}$, $T_{304}$. The force detection lattice unit $T_{F1}$ is not formed in a different way from the refraction lattice units $T_{301}$, $T_{302}$, $T_{303}$, $T_{304}$, but just its location and lattice interval are different therefrom. Even though the front end portion of the FBG sensor 300 is mostly confined by the body 10, its front end 361 protrudes forwards in comparison to the front end of the body 10.

The principle of detecting a force applied to the FBG sensor 300 by means of the force detection lattice unit $T_{F2}$ is identical to the above description.

The force information respectively detected at two FBG sensors 200, 300 may be averaged and used as average force information applied to the body 10, and the force information may also be used to obtain local force information of the front end of the body 10.

Strains of the force detection lattice units of two FBG sensors 200, 300 also include an influence caused by a temperature variation applied to the front end portions of the FBG sensors 200, 300.

Therefore, according to this embodiment, an error caused by the temperature variation of the front end portion of the FBG sensors 200, 300 may be corrected by calculating strains £ of the force detection lattice units $T_{F1}$, $T_{F2}$ of two FBG sensors 200, 300 first and then reducing the strain $\varepsilon_T$ of the temperature detection lattice unit $T_T$ of the FBG sensor 100 from the above value.

At this time, the temperature detection lattice unit $T_T$ of the FBG sensor 100 should be corrected in consideration of a value corresponding to the strains applied to the force detection lattice units $T_{F1}$, $T_{F2}$ of the FBG sensors 200, 300 due to the confinement of the body 10, because the lattice interval is changed without a confining force of the body 10 and the force detection lattice units $T_{F1}$, $T_{F2}$ of the FBG sensors 200, 300 change lattice intervals while being confined to the body 10.

According to this embodiment, at least one of refraction information of the body, force information applied to the body and temperature information of the body may be selectively extracted using the FBG sensor provided at a single sensor assembly 1".

Therefore, the sensor assembly 1" may be suitably used for a guide wire or the like, which guides a surgical instrument such as a catheter into a living body tissue such as a blood vessel.

When the guide wire is introduced into a blood vessel, an accurate three-dimensional location of the guide wire in the blood vessel may be calculated by comparing information of the blood vessel, which has been scanned in advance, and the refraction information of the body and the force information applied to the body, which are obtained by means of the sensor assembly 1".

Therefore, it is possible to prevent the guide wire (the body 10 of the sensor assembly 1") from being damaging the blood vessel, thereby promoting stability in surgical proceedings.

According to this embodiment, the FBG sensor 100 simultaneously serves as a refraction-detecting FBG sensor for detecting refraction information and a temperature-detecting FBG sensor for detecting temperature information, and the FBG sensors 200, 300 simultaneously serve as a refraction-detecting FBG sensor for detecting refraction information and a force-detecting FBG sensor for detecting force information, without being limited thereto.

Figure 10:
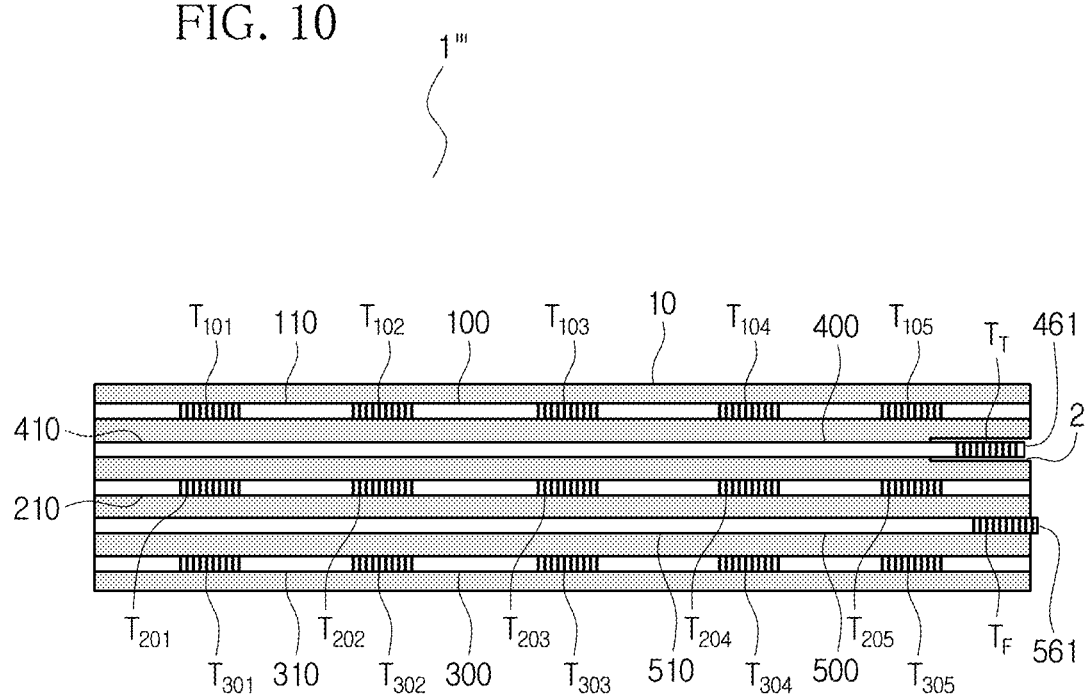
FIG. 10 is a side view showing a sensor assembly according to another embodiment of the present disclosure.
Figure 11:
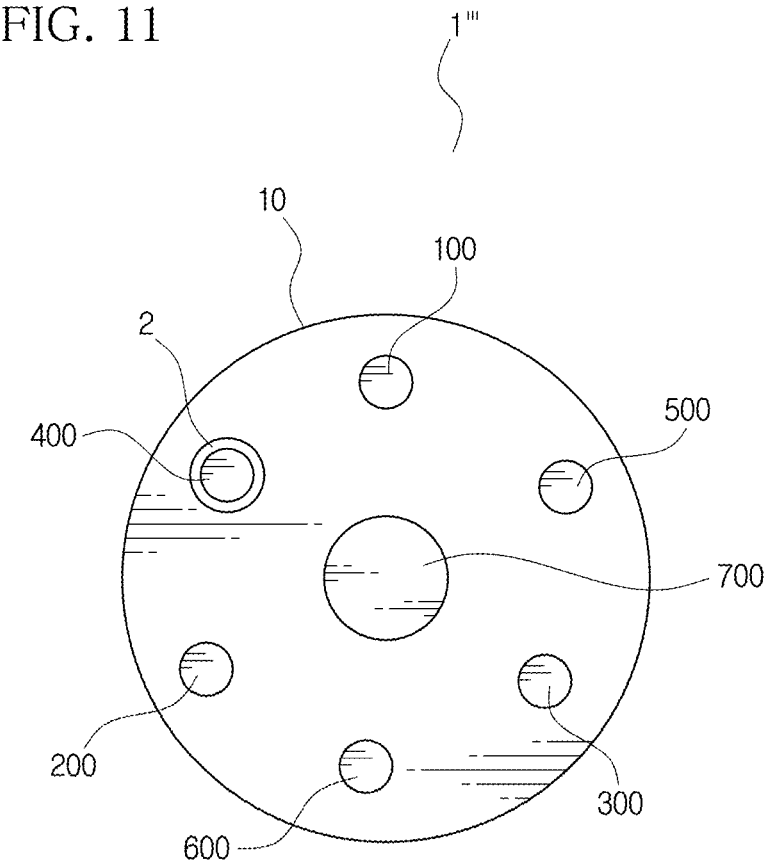
FIG. 11 is a front view showing the sensor assembly of FIG. 10.

FIG. 10 is a side view showing a sensor assembly 1''' according to another embodiment of the present disclosure, and FIG. 11 is a front view showing the sensor assembly 1'''.

The sensor assembly 1''' of this embodiment includes three refraction-detecting FBG sensors 100, 200, 300, a temperature-detecting FBG sensor 400 and a force-detecting FBG sensor 500.

A plurality of refraction lattice units $T_{101}$, $T_{102}$, $T_{103}$, $T_{104}$, $T_{105}$ is formed in the middle of the optical fiber 110 of the FBG sensor 100. Lattices forming each of the refraction lattice units $T_{101}$, $T_{102}$, $T_{103}$, $T_{104}$, $T_{105}$ are disposed with the same interval. Intervals between lattices respectively forming each of the refraction lattice units $T_{101}$, $T_{102}$, $T_{103}$, $T_{104}$, $T_{105}$ are different from each other and are gradually increasing in this embodiment.

A plurality of refraction lattice units $T_{201}$, $T_{202}$, $T_{203}$, $T_{204}$, $T_{205}$ is formed in the middle of the optical fiber 210 of the FBG sensor 200. Lattices each of the refraction lattice units $T_{201}$, $T_{202}$, $T_{203}$, $T_{204}$, $T_{205}$ are disposed with the same interval. Intervals between lattices respectively forming each of the refraction lattice units $T_{201}$, $T_{202}$, $T_{203}$, $T_{204}$, $T_{205}$ are different from each other and are gradually increasing in this embodiment.

A plurality of refraction lattice units $T_{301}$, $T_{302}$, $T_{303}$, $T_{304}$, $T_{305}$ is formed in the middle of the optical fiber 310 of the FBG sensor 300. Lattices each of the refraction lattice units $T_{301}$, $T_{302}$, $T_{303}$, $T_{304}$, $T_{305}$ are disposed with the same interval. Intervals between lattices respectively forming each of the refraction lattice units $T_{301}$, $T_{302}$, $T_{303}$, $T_{304}$, $T_{305}$ are different from each other and are gradually increasing in this embodiment.

Refraction information of the body 10 may be detected from a wavelength spectrum of reflected lights output from three FBG sensors 100, 200, 300.

A lattice unit is not formed in the middle of the optical fiber 410 of the FBG sensor 400, and a temperature detection lattice unit $T_T$ composed of at least two lattices is formed at the front end portion exposed to the concave groove 2.

The FBG sensor 400 becomes a dedicated sensor for detecting only temperature information of the body 10 by analyzing the wavelength spectrum of the reflected light by the temperature detection lattice unit $T_T$.

A lattice unit is not formed in the middle of the optical fiber 510 of the FBG sensor 500, and a force detection lattice unit $T_F$ composed of at least two lattices is formed at the front end portion.

The FBG sensor 500 becomes a dedicated sensor for detecting only force information applied to the body 10 by analyzing the wavelength spectrum of the reflected light by the force detection lattice unit $T_F$.

According to this embodiment, the sensor assembly 1''' separately includes a refraction-detecting FBG sensor, a temperature-detecting FBG sensor and a force-detecting FBG sensor. Therefore, information interference of the reflected lights output from the FBG sensors become minimized, and the sensor assembly 1''' may be used for more diverse purposes since dedicated FBG sensors may be selectively disposed as necessary.

According to this embodiment, refraction information of the body 10 is obtained using three FBG sensors, without being limited thereto. It would be understood that refraction information such as curvature and curved angle of the body 10 may be detected by applying the principle described above, if at least two refraction-detecting FBG sensors as described above are provided.

In this embodiment, a sensor assembly capable of extracting at least one of, force information applied to the body 10 and/or temperature information of the body 10 together with refraction information of the body 10 by using the FBG sensors has been described, but the present disclosure is not limited thereto.

Referring to FIG. 1 again, the sensor assembly 1 of this embodiment may further include a laser-irradiating optical fiber 700 formed in the middle of the body 10, in addition to three refraction-detecting FBG sensors 100, 200, 300, the temperature-detecting FBG sensor 400 and the force-detecting FBG sensor 500.

The laser-irradiating optical fiber 700 transmits a laser irradiated through a laser light source (not shown) to a target.

The sensor assembly 1 having the laser-irradiating optical fiber 700 may be not only used for simply guiding an instrument such as a catheter like a guide wire in a narrow passage like a blood vessel but also used as an instrument for embolic treatment or atheroma removal, which makes tissues die by laser.

Moreover, the sensor assembly 1 may further include a flow sensor 600 for detecting flow rate information of fluid (blood) which flows in a work environment at which the body 10 is located, for example an inside of a blood vessel. The flow sensor 600 includes a flow rate-detecting optical fiber 610.

The light passing through the flow rate-detecting optical fiber 610 and reflected by the fluid exhibits so-called "Doppler effect", similar to sound wave. In other words, if the flow rate increases or becomes strong, a wavelength of the reflected light is changed. If this Doppler effect of light is used, flow rate information of the fluid may be detected. The flow rate detecting method using an optical fiber is already known in the art and thus not described here in detail.

The sensor assembly 1 including the flow sensor 600 may be used as a guide wire for balloon angioplasty which guides a balloon catheter into a blood vessel.

After the balloon angioplasty is performed, it may be found whether the surgical procedure is successful, by analyzing a blood flow by means of the flow rate-detecting optical fiber 600.

According to this embodiment, it is possible to form a sensor assembly selectively having various functions by using optical fibers, which can be easily fabricated, and thus ensures various applications.

Moreover, a plurality of sensors may be implemented in a minute diameter, and a sensor assembly with deep flexion may be fabricated.

What is claimed is:

1. A sensor assembly, comprising:
   a flexible body; and
   fiber Bragg grating (FBG) sensors disposed inside the flexible body,
   wherein the FBG sensors each comprise an optical fiber extending axially with respect to the flexible body, and lattices disposed in the optical fiber,
   wherein the FBG sensors comprise a force-detecting FBG sensor, and
   wherein a front end of the force-detecting FBG sensor protrudes from a front end face of the flexible body such that a lattice of the force-detecting FBG sensor is exposed.

2. The sensor assembly according to claim 1,
   wherein the FBG sensors comprise a temperature-detecting FBG sensor, and
   wherein a front end of the temperature-detecting FBG sensor is recessed from the front end face of the flexible body.

3. The sensor assembly according to claim 1,
   wherein the FBG sensors comprise a temperature-detecting FBG sensor, and
   wherein a front end of the temperature-detecting FBG sensor is disposed inside a recess of the flexible body such that the front end of the temperature-detecting FBG sensor does not contact the flexible body,
   wherein the recess is in fluid communication with an exterior of the flexible body.

4. The sensor assembly according to claim 3,
   wherein a lattice of the temperature-detecting FBG sensor is disposed inside the recess.

5. The sensor assembly according to claim 3,
   wherein a diameter of the recess is greater than a diameter of the temperature-detecting FBG sensor.

6. The sensor assembly according to claim 1,
   wherein the FBG sensors comprise a temperature-detecting FBG sensor for detecting the temperature information, and
   wherein a temperature detection lattice unit comprising at least two lattices with a same interval is formed at a front end portion of the temperature-detecting FBG sensor.

7. The sensor assembly according to claim 1,
   wherein the lattice is formed with a uniform lattice interval.

8. The sensor assembly according to claim 1,
   wherein the FBG sensors comprise at least three refraction-detecting FBG sensors for detecting the refraction information,
   wherein a plurality of lattices is formed at the refraction-detecting FBG sensor over the entire length of the optical fiber,
   wherein an n (n≥2, natural number) number of the plurality of lattices are grouped to form a plurality of refraction lattice units,
   wherein an n number of lattices are disposed with a same interval in a single refraction lattice unit among the plurality of refraction lattice units, and
   wherein the refraction lattice units have different intervals between lattices from each other.

9. The sensor assembly according to claim 8,
   wherein the at least three refraction-detecting FBG sensors are disposed eccentrically from a central axis of the flexible body.

10. The sensor assembly according to claim 1, wherein the FBG sensors further comprise
    a temperature-detecting FBG sensor,
    and
    at least three refraction-detecting FBG sensors.

11. The sensor assembly according to claim 1,
    wherein the FBG sensors comprise at least three refraction-detecting FBG sensors for detecting refraction information,
    wherein at least one of the at least three refraction-detecting FBG sensors constitute a temperature-detecting FBG sensor for detecting temperature information, and
    wherein at least another one of the at least three refraction-detecting FBG sensors constitutes the force-detecting FBG sensor, which is for detecting the force information.

12. The sensor assembly according to claim 1, further comprising
    a laser-irradiating optical fiber disposed inside the flexible body and configured to conduct laser light.

13. The sensor assembly according to claim 1, further comprising
    a flow-detecting FBG sensor disposed inside the flexible body.

14. A sensor assembly, comprising:
    a flexible body; and
    fiber Bragg grating (FBG) sensors disposed inside the flexible body, and comprising a temperature-detecting FBG sensor,
    wherein the FBG sensors each comprise an optical fiber extending axially with respect to the flexible body, and lattices disposed in the optical fiber, and
    wherein a front end of the temperature-detecting FBG sensor is disposed inside a recess of the flexible body open to an exterior of the flexible body.

15. The sensor assembly of claim 14,
    wherein the temperature-detecting FBG sensor does not contact an interior surface of the recess.

16. The sensor assembly of claim 15,
    wherein a lattice of the temperature-detecting FBG sensor is disposed inside the recess and retruded from an end face of the flexible body.

* * * * *